United States Patent [19]
Storch et al.

[11] Patent Number: 5,877,232
[45] Date of Patent: Mar. 2, 1999

[54] RESINOUS DENTAL COMPOSITION BASED ON POLYMERISABLE POLYSILOXANES

[75] Inventors: Werner Storch, Würzburg; Herbert Wolter, Gerchsheim-Grossrinderfeld, both of Germany

[73] Assignee: The Procter & Gamble Company, Cincinnati, Ohio

[21] Appl. No.: 712,653

[22] Filed: Sep. 13, 1996

Related U.S. Application Data

[63] Continuation of Ser. No. 211,479, filed as PCT/US92/08530, Oct. 7, 1992, abandoned.

[30] Foreign Application Priority Data

Oct. 9, 1991 [DE] Germany .......................... 41 33 494.9

[51] Int. Cl.$^6$ .......................... C08F 230/08; C08G 77/06
[52] U.S. Cl. .......................... 523/116; 526/279; 528/13; 528/14; 528/16; 528/17; 528/19; 528/950; 433/228.1
[58] Field of Search .......................... 523/116; 528/950, 528/13, 14, 16, 17, 19; 433/228.1; 526/279

[56] References Cited

U.S. PATENT DOCUMENTS

| | | | |
|---|---|---|---|
| 3,127,363 | 3/1964 | Nitzsche et al. | 433/228.1 |
| 4,308,014 | 12/1981 | Kawahara et al. | 433/228.1 |
| 4,359,565 | 11/1982 | Puppe et al. | 528/15 |
| 4,368,314 | 1/1983 | Endo et al. | 528/89 |
| 4,504,231 | 3/1985 | Koblitz et al. | 523/116 |
| 4,599,155 | 7/1986 | Suzuki et al. | 522/8 |
| 4,673,354 | 6/1987 | Culler | 433/217.1 |
| 4,843,136 | 6/1989 | Reiners et al. | 526/279 |
| 5,399,738 | 3/1995 | Wolter et al. | 556/429 |
| 5,414,093 | 5/1995 | Wolter | 549/214 |
| 5,532,398 | 7/1996 | Wolter et al. | 556/420 |

FOREIGN PATENT DOCUMENTS

| | | | |
|---|---|---|---|
| 29 22 932 A1 | 12/1979 | Germany | C07F 7/18 |
| 2922932 | 12/1979 | Germany | C07F 7/21 |

*Primary Examiner*—Andrew E. C. Merriam
*Attorney, Agent, or Firm*—Mary Catherine Hentz; Douglas C. Mohl; Jacobus C. Rasser

[57] ABSTRACT

The invention relates to a self-curing, photochemically or thermally curable resinous dental composition based on polymerisable polysiloxanes, to a process for its preparation and to its use for the preparation of pasty, self-curing, photochemically or thermally curable dental materials. Said composition is obtainable by hydrolytic condensation of one or more hydrolytically condensable silicon compounds, 1 to 100 mol %, based on monomeric compounds, of silanes of the general formula: $Y^n\text{-}SiX_mR_{4-(n+m)}$ and/or $\{X_nR_kSi[R^2(A)_l]_{4-(n+k)}\}_xB$ being selected. The radicals A, X, Y, $R^2$, R' and R are identical or different and have the following meaning: A=O, S, PR', POR', NHC(O)O or NHC(O)ONR', B=a straight-chain or branched organic radical which is derived from a compound B' having at least one (for l=1 and A=NHC(O)O or NHC(O)NR') or at least two C=C double bonds and 5 to 50 carbon atoms, R=alkyl, alkenyl, aryl, alkylaryl or arylalkyl, R'=H, alkyl or aryl, $R^2$=alkylene, arylene or alkylenearylene, X=H, halogen, hydroxyl, alkoxy, acyloxy, alkylcarbonyl, alkoxycarbonyl or $NR'_2$, Y=a substituent which contains a substituted or unsubstituted 1,4,6-trioxaspiro[4.4]nonane radical, n=1, 2 or 3, m=1, 2 or 3, where n+m≦4, k=0, 1 or 2, l=0 or 1, x=an integer whose value is stated in the description.

22 Claims, No Drawings

RESINOUS DENTAL COMPOSITION BASED ON POLYMERISABLE POLYSILOXANES

This is a continuation of application Ser. No. 08/211,479, filed as PCT/US92/08530, Oct. 7, 1992, now abandoned.

The invention relates to a resinous dental composition, which is self-curing, photochemically or thermally curable in the presence of initiators, based on polymerisable polysiloxanes, to a process for its preparation and to its use for the preparation of pasty dental materials, which are self-curing, photochemically or thermally curable in the presence of initiators, which are composed of one or more resinous dental compositions and optionally of one or more finely divided fillers and/or customary additives. Suitable additives are, for example, pigments, stabilisers, plasticisers or impact strength enhancers.

The term "dental material" includes, for example, filling materials for looking after carious defects or other dental defects in the oral cavity, inlays, crown and bridge materials, facings, sealing and protective coating compositions, synthetic fixing materials for fixing inlays or crowns and bridges, stump building-up materials, prosthetic materials, compositions for the production of artificial teeth, and adhesion promoters for dental filling materials.

Customary resinous dental compositions as a rule function as binders for the production of dental materials and contain at least one monomeric ester of methacrylic acid, but usually a mixture of several such esters. Suitable monofunctional esters of methacrylic acid are, for example, methyl methacrylate, ethyl methacrylate, isopropyl methacrylate, n-hexyl methacrylate and 2-hydroxyethyl methacrylate.

Recently, polyfunctional esters of methacrylic acid with relatively high molecular weights have commonly been employed, such as, for example, ethylene glycol dimethacrylate, butanediol 1,4-dimethacrylate, triethylene glycol dimethacrylate, dodecanediol-1,12-dimethacrylate, dodecanediol 1,10-dimethacrylate, pentaerythritol trimethacrylate, pentaerythritol tetramethacrylate, trimethylolpropane trimethacrylate, 2,2-bis(p-($\gamma$-meth-acryloxy-$\beta$-hydroxypropoxy)-phenyl)-propane, 2,2-bis(p-($\beta$-hydroxyethoxy)-phenyl)propane dimethacrylate (bis-GMA), the diadduct of hydroxyethyl methacrylate and trimethylhexamethylene diisocyanate and the diadduct of hydroxyethyl methacrylate and isophorone diisocyanate.

Materials based on, for example, methyl methacrylate, which are used as prosthetic bases, crown and bridge resins or as filling resins, do present outstanding advantages with respect to their workability, their aesthetic appearance, their stability in the oral area etc. However, since these materials have poor mechanical strengths, it may happen that a breakage occurs in the production of a prosthesis after polymerisation in a plaster of Paris mould during removal from this mould, that the prosthesis breaks in the mouth or if it is unintentionally dropped. In view of the sensitivity to temperature and taste and the strange feel in the employed state, it is expedient if a prosthesis is kept as thin as possible. However, it is virtually impossible to make it thin because of its strength.

When using the above mentioned materials as crown and bridge resin, there is the risk owing to the poor abrasion resistance that the sensitive surface will be abraded by brushing etc. or the cutting edge will break off. To eliminate these disadvantages experiments have been undertaken to improve the mechanical strength of such dental materials by means of novel resin formulations. Thus, resinous dental compositions based on polysiloxane polymers which are copolymerized with further monomers are disclosed in DE 3,610,804 A1, which should lead after polymerisation to compositions having improved resistance to pressure, abrasion resistance, flexural strength etc. The disadvantage of these resinous dental compositions, however, is their large shrinkage on curing, which does not permit their use in many application areas.

Depending on the application purpose, materials for dental applications can be cured in various ways. There are dental filling materials both as photochemically curing and as self-curing (autopolymerising) compositions. The photochemically curing compositions contain photoinitiators such as benzoin alkyl ethers, benzil monoketals, acylphosphine oxides or aliphatic or aromatic 1,2-diketo compounds, such as, for example, camphorquinone, and polymerisation accelerators such as aliphatic or aromatic tertiary amines, for example N,N-dimethyl-p-toluidine or triethanolamine, or organic phosphites, and cure on irradiation with UV or visible light.

The self-curing dental materials are composed as a rule of a catalyst and a base paste, each of which contains the component of a redox system, and which polymerise on mixing both components. One component of the redox system is usually a peroxide, such as, for example, dibenzoyl peroxide, the other is usually a tertiary aromatic amine, such as, for example, N,N-dimethyl-p-toluidine.

Other dental materials such as prosthetic plastics or synthetic compositions for the production of artificial teeth can be polymerised under the action of heat. Initiators used here are as a rule peroxides such as dibenzoyl peroxide, dilauryl peroxide or bis(2,4-dichlorobenzoyl peroxide).

Dental materials furthermore as a rule contain pigments which—added in a small amount—are used to bring the colour of the dental materials into line with the various shadings of natural teeth. Suitable pigments are, for example, iron oxide black, iron oxide red, iron oxide yellow, iron oxide brown, zinc oxide and titanium oxide.

Dental materials usually also contain organic or inorganic fillers. This is done in order to reduce the shrinkage in volume of the resinous dental composition during polymerisation. Pure, monomeric methyl methacrylate shrinks, for example, during polymerization by about 20% by volume. By addition of about 60% by weight of solid methyl methacrylate polymer, the shrinkage can be reduced to about 5 to 7% by volume (DE Patent 2,403,211).

Other organic fillers are obtained by preparing a polymer which is essentially composed of methacrylic acid esters and is non-crosslinked or crosslinked. This polymer optionally contains surface-treated fillers. If it is prepared as a polymer, it can be added to the resinous dental composition in this form; on the other hand if it is prepared in compact form by polymerisation in substance, it must first be ground to give a so-called chip polymer before incorporation in the resinous dental composition.

In addition to the already-mentioned filler-containing bead and chip polymers, commonly used preformed polymers are homopolymers of methyl methacrylate or, preferably non-crosslinked, copolymers of methyl methacrylate having a low content of esters of methyacrylic acid or of acrylic acid with 2 to 12 C atoms in the alcohol component, expediently in the form of a bead polymer. Other suitable polymers are non-crosslinked products based on polyurethanes, polycarbonates, polyesters and polyethers.

Thus, for example, in DE 3,903,407 C2 dental filling materials based on polymerisable (meth)acrylic acid esters are disclosed as a resinous dental composition, i.e. as binders which contain finely ground inorganic/organic polymers based on polysiloxanes as fillers. For the preparation of dental filling materials, these inorganic/organic polymers are added in finely ground form to the resinous dental composition, together with other components, as a filler.

Inorganic fillers are, for example, finely ground glasses or quartz having mean particle sizes between about 1 and 10 µm and highly disperse SiO2 having mean particle sizes between about 10 and 400 nm. The glasses are preferably aluminium silicate glasses, which can be doped with barium, strontium or rare earths (DE Patent 2,458,380).

With respect to the finely ground quartz and the highly disperse SiO2, it remains to be noted that the inorganic filler is as a rule silanised before mixing with the monomers for better binding to the organic matrix. For this purpose, the inorganic fillers are coated with silane coupling agents (as adhesion promoters) which usually have a polymerisable double bond for reaction with the monomeric esters of methacrylic acid. Suitable silane coupling agents are, for example, vinyl trichlorosilane, tris(2-methoxyethoxy)vinylsilane, tris(acetoxy)vinylsilane and 3-methacryloyloxypropyl-trimethoxysilane.

The filling materials composed of fillers and polymerisable compounds, the so-called "composites", have in particular recently gained increasing importance in dental medicine. These are composed of an inorganic or organic filler and of a curable organic matrix. In this way, the fillers cause a decrease in the shrinkage on polymerisation of the resultant dental material and a reinforcement of the organic polymer structure. Very generally, it can be said that improved mechanical properties and a reduced shrinkage on curing can be achieved by as high a content as possible of fillers in the dental materials. The highest amount of fillers to be employed is dependent, however, on the properties of the monomers employed in the resinous dental composition.

Good mechanical properties and high resistances to abrasion are important requirements which must be aimed at by a dental material which is intended permanently to replace lost dental enamel. In addition to these reinforcing properties, other material parameters must likewise also be aimed at by dental materials. In this connection, an essential parameter is the polishing ability. High gloss polishing ability is of considerable importance for dental filling materials as well as for bridge and crown materials for at least two reasons:

For aesthetic reasons, a highly glossy and completely homogeneous surface of the filling material is to be required in order that the filling can no longer be differentiated from the surrounding, absolutely smooth, natural dental enamel. Furthermore, this highly glossy filling surface must retain its character long-term. A highly smooth filling surface is therefore also important in order that plaque or discolouring media do not find any mechanical anchorage sites.

In the customary dental materials, the property of high gloss polishing ability is produced by the addition of fillers, since the customary resinous dental compositions employed as binders are not polishable after their curing. Thus, DE 3,913,250 A1 and DE 3,913,252 A1 disclose dental materials which are curable to give a composition which can be polished to a high gloss. This high gloss polishing ability is achieved by the addition of finely divided organopolysiloxanes as a filler.

Polymer composites and amalgams are two important classes of material in the restorative dental field. on the basis of toxicological considerations, the desire is to replace amalgam fillings by composite materials. Commercially available dental composites as a rule additionally exhibit the following weak points:

too great a shrinkage on curing, too high a thermal expansion coefficient in comparison with the dental tissue inadequate adhesion to the dental tissue These deficiencies can lead to formation of a gap at the edge and to secondary caries, and thus further reduce the stability of the filling over time.

A further weak point of the conventional composite materials is their poor abrasion behaviour.

The recently used polyfunctional monomeric esters of methacrylic acid mentioned at the beginning do cause a decrease in the shrinkage on polymerisation and the shrinkage on polymerisation can be still further reduced by addition of up to about 85% by weight of the described fillers, but the reduction of the shrinkage on curing thus obtainable is not adequate in order to be aimed at all requirements of an optimum dental filling material. The same applies to the resinous dental compositions based on polysiloxane polymers mentioned at the beginning. With conventional polymer systems containing inorganic fillers, a reduction in the shrinkage below 2% is barely possible. Therefore optimal sealing at the edge with dental fillings is only achievable by means of energy-consuming inlay technique.

In addition, a reduction of the thermal expansion coefficients below about $25 \times 10^{-6}$ $K^{-1}$ is not possible with the conventional composite materials. This value is much too high to ensure a sufficiently good temperature change behaviour of the resulting dental material, in particular of dental fillings, since the thermal expansion coefficient of the dental enamel or of the dentine is about $12 \times 10^{-6}$ $K^{-1}$. The thermal expansion coefficient of the resulting dental filling is dependent on the filler contents, since fillers as a rule have a lower expansion coefficient than the organic matrix.

Further requirements which are made of a dental material and in particular of a dental filling material are its X-ray opacity and its adhesion to enamel and to dentine, where the adhesive force to enamel and to dentine should be larger than the shrinkage forces. With the conventional dental materials, the X-ray opacity is set by the type and amount of the fillers and it is usually achieved by addition of Ba, Sr, Ti or Zr components. With the conventional dental materials, the adhesive force to dentine is inadequate even when using dentine adhesives.

The object of the present invention was therefore to make available a resinous dental composition which is self-curing, thermally or photochemically curable, which is simple to process, which on curing undergoes no shrinkage in volume or only a slight shrinkage in volume and which after curing even without addition of fillers should have the following properties:

a high resistance to abrasion, a high dimensional stability, a low thermal expansion coefficient, a high radioopacity, a large adhesion force to enamel and dentine and a good polishing ability.

These resinous dental compositions should either be employable as such as dental materials, or they should be able to be processed to give the dental materials mentioned at the beginning, with the addition of further components, such as, for example, of further resinous compositions, or of fillers, pigments, initiators, stabilisers, plasticisers or impact strength enhancers. In addition, the resinous dental compositions should be employable as or in mono- or multicomponent systems.

This object is achieved by resinous dental compositions based on polymerisable polysiloxanes, which are self-curing, photochemically or thermally curable in the presence of one or more initiators, and which are obtainable by hydrolytic condensation of one or more hydrolytically condensable compounds of silicon and if desired other elements of the group comprising B, Ba, Ti, Zr, Al, Sn, the transition metals, the lanthanides and the actinides, and/or precondensates derived from the abovementioned compounds, if appropriate in the presence of a catalyst and/or of a solvent, by the action of water or moisture, 1 to 100 mol %, preferably 5 to 100 mol %, based on monomeric compounds, of silanes of the general formula (I)

$$Y_nSiX_mR_{4-(n+m)} \qquad (I)$$

being selected in which the radicals X, Y and R are identical or different and have the following meaning:

R=alkyl, alkenyl, aryl, alkylaryl or arylalkyl,

X=hydrogen, halogen, hydroxyl, alkoxy, acyloxy, alkylcarbonyl, alkoxycarbonyl or NR'$_2$, where R'=hydrogen, alkyl or aryl, Y=a substituent which contains a substituted or unsubstituted 1,4,6-trioxaspiro(4.4)nonane radical, n=1, 2 or 3, m=1,2 or 3, where n+m≦4, and/or of silanes of the general formula (II)

$$\{X_nR_kSi(R^2(A)_{4-(n+k)}\}_xB \qquad (II)$$

in which the radicals A, R, R$^2$ and X are identical or different and have the following meaning:

A=O, S, PR', POR', NHC(O)O or NHC(O)ONR', where R'=hydrogen, alkyl or aryl,

B=a straight-chain or branched organic radical which is derived from a compound B' having at least one (for l=1 and A=NHC(O)O or NHC(O)NR') or at least two C=C double bonds and 5 to 50 carbon atoms, where R'=hydrogen, alkyl or aryl, R=alkyl, alkenyl, aryl, alkylaryl or arylalkyl, R2=alkylene, arylene or alkylenearylene, X=hydrogen, halogen, hydroxyl, alkoxy, acyloxy, alkylcarbonyl, alkoxycarbonyl or NR'2, where R'=hydrogen, alkyl or aryl, n=1, 2 or 3, k=0, 1 or 2, l=0 or 1, x=an integer whose maximum value corresponds to the number of double bonds in the compound B' minus 1, or is equal to the number of double bonds in the compound B' when l=1 and A represents NHC(O)O or NHC(O)NR'.

Surprisingly, it has now been found that the resinous dental compositions according to the invention form polymers after curing thereof and even without addition of fillers, which have excellent resistances to abrasion and dimensional stabilities, which have low thermal expansion coefficients and high radioopacities, and which exhibit a very large adhesive force to enamel and dentine and very good polishing abilities. In addition, it has surprisingly been found that the resinous dental compositions according to the invention, depending on the silanes employed, undergo only a very low, no or even a negative shrinkage in volume on curing.

These properties, which are so important for dental materials, can be still further improved by addition of customary fillers, so that with the aid of the resinous dental compositions according to the invention dental materials can be prepared which with respect to the abovementioned properties represent a very considerable improvement in the prior art.

The silanes of the general formulae (I) and (II) are hydrolysable and polymerisable, the radicals X being hydrolysable and the radicals B and Y being polymerisable and in each case at least one radical B, X and Y having the abovementioned meaning being present in the silanes of the general formulae (I) and (II).

The alkyl radicals are, for example, straight-chain, branched or cyclic radicals having 1 to 20, preferably having 1 to 10, carbon atoms, and particularly preferably are lower alkyl radicals having 1 to 6 carbon atoms. Specific examples are methyl, ethyl, n-propyl, i-propyl, n-butyl, s-butyl, t-butyl, i-butyl, n-pentyl, n-hexyl, cyclohexyl, 2-ethylhexyl, dodecyl and octadecyl.

The alkenyl radicals are, for example, straight-chain, branched or cyclic radicals having 2 to 20, preferably having 2 to 10, carbon atoms, and particularly preferably are lower alkenyl radicals having 2 to 6 carbon atoms, such as, for example, vinyl, allyl or 2-butenyl.

Preferred aryl radicals are phenyl, biphenyl and naphthyl. The alkoxy, acyloxy, alkylcarbonyl, alkoxycarbonyl and amino radicals are preferably derived from the abovementioned alkyl and aryl radicals. Specific examples are methoxy, ethoxy, n- and i-propoxy, n-, i-, s- and t-butoxy, methylamino, ethylamino, dimethylamino, diethylamino, N-ethylanilino, acetoxy, propionyloxy, methylcarbonyl, ethylcarbonyl, methoxycarbonyl, ethoxycarbonyl, benzyl, 2-phenylethyl and tolyl.

The said radicals can optionally carry one or more substituents, for example halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxyl, formyl, carboxyl, mercapto, cyano, isocyanato, nitro, epoxy, SO$_3$H and PO$_4$H$_2$.

Among the halogens, fluorine, chlorine and bromine are preferred.

The substituted or unsubstituted 1,4,6-trioxaspiro(4.4) nonane groups are bonded to the Si atom via alkylene or via alkenylene radicals, which can be interrupted by ether or ester groups. Specific examples and preferred embodiments of the radicals Y are

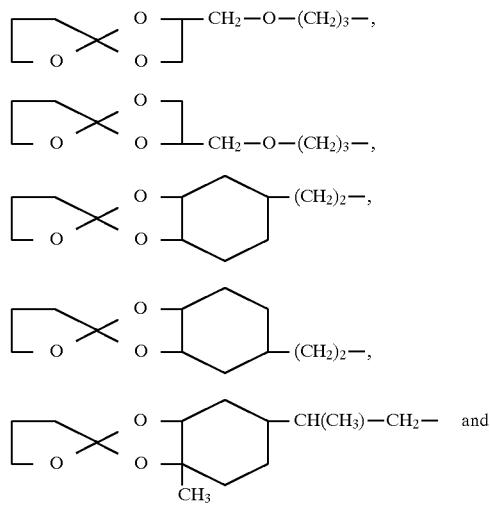

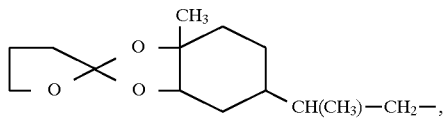
where the ring system, which is derived from γ-butyrolactone, can also be substituted as shown in Claim 2. The substituents can be hydrogen, halogen or hydroxyl, alkyl, alkenyl, aryl, alkylaryl, arylalkyl, alkylcarbonyl or alkoxycarbonyl groups. Actual examples of these are
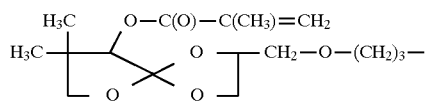
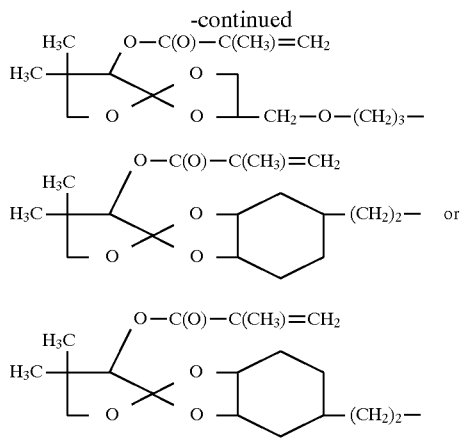
Actual examples of silanes of the formula (I) are:
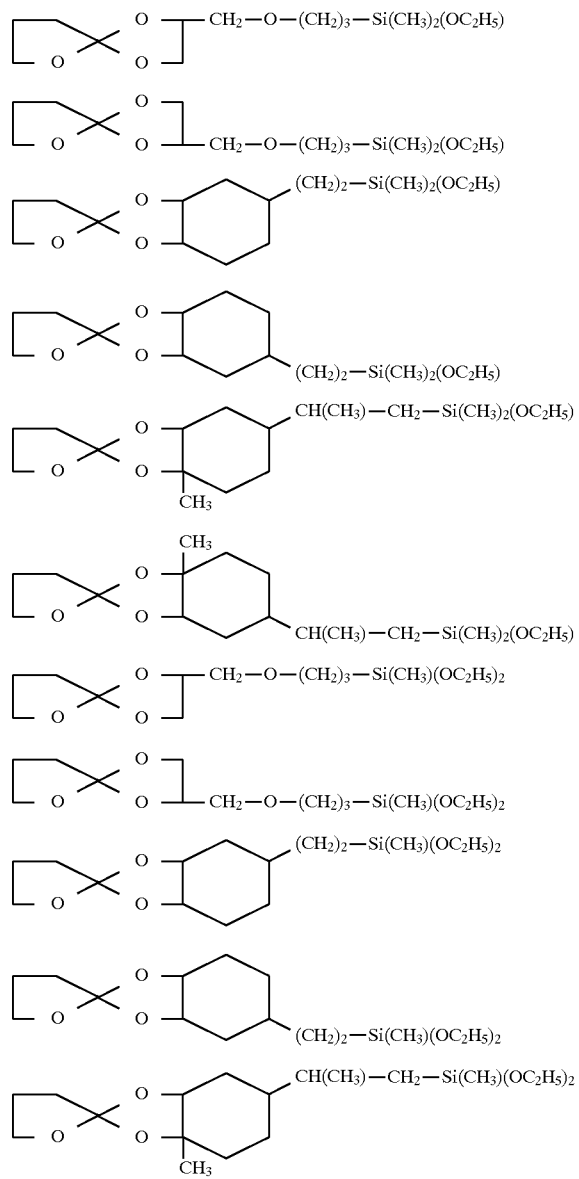

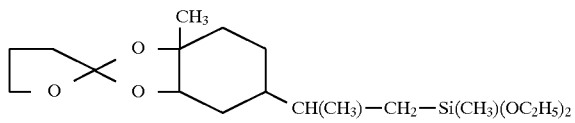
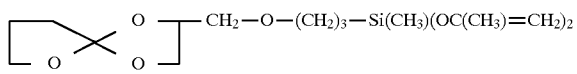
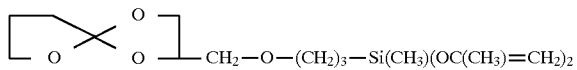
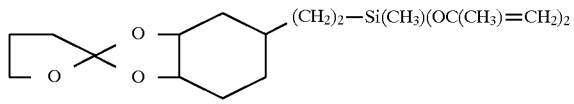
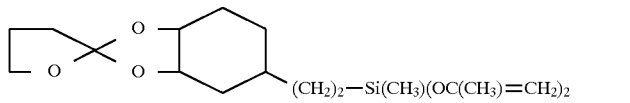
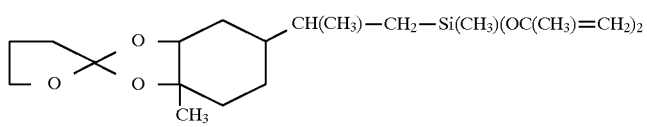
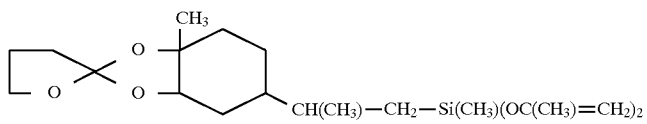
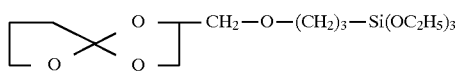
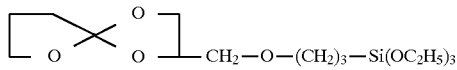
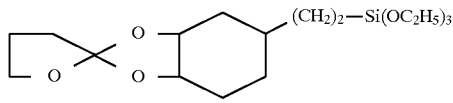
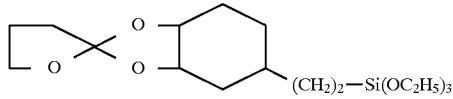
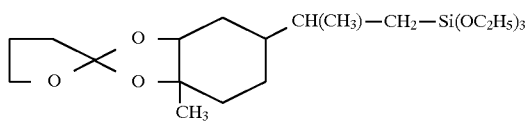
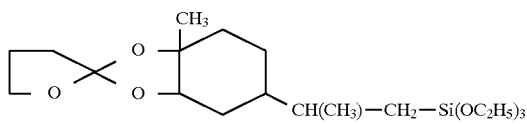
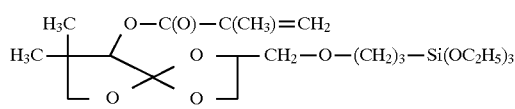
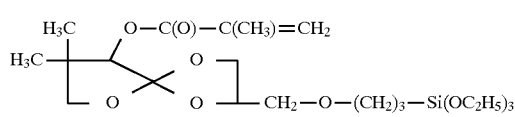

-continued
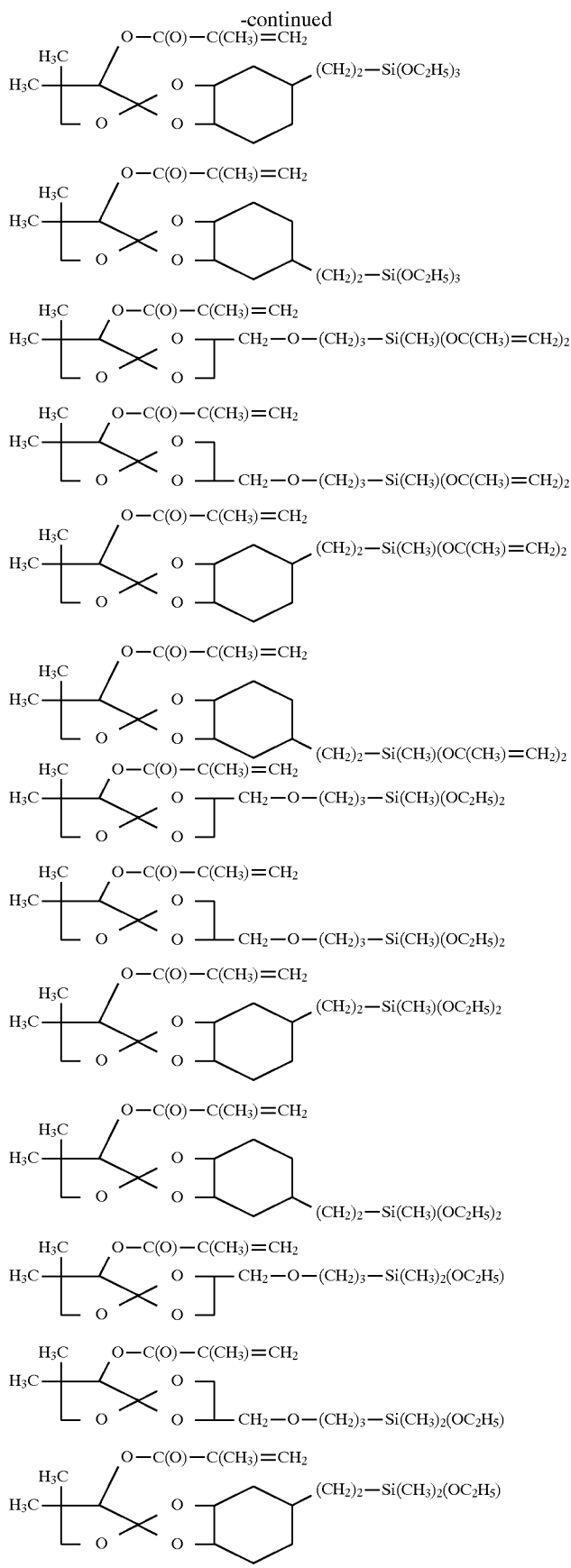

-continued
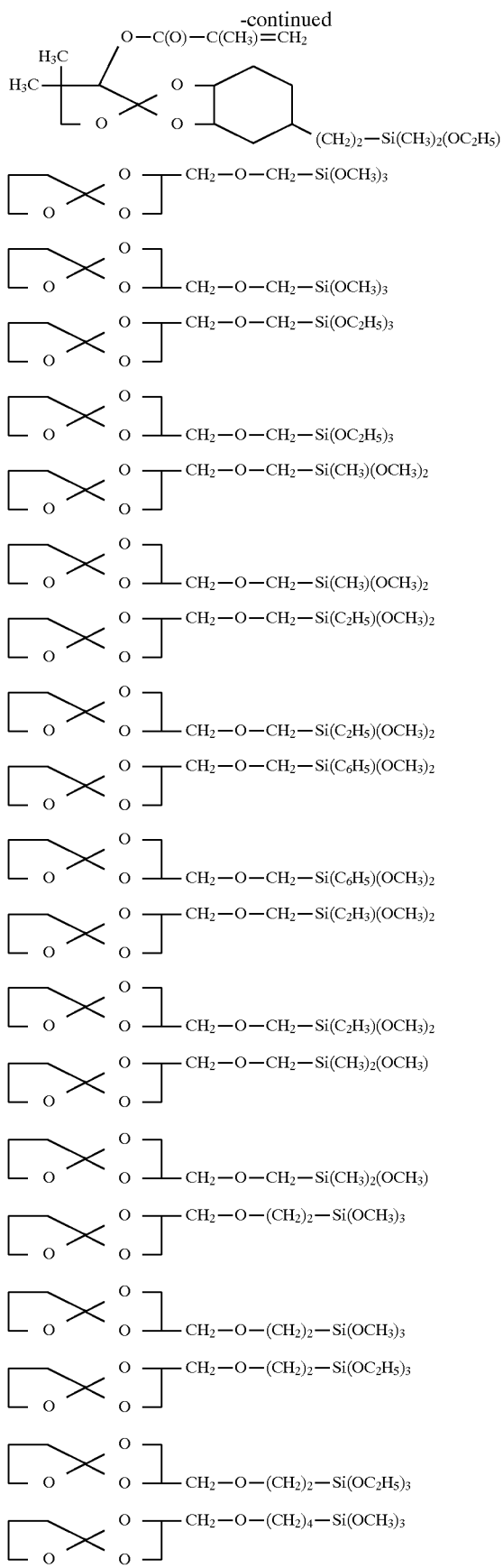

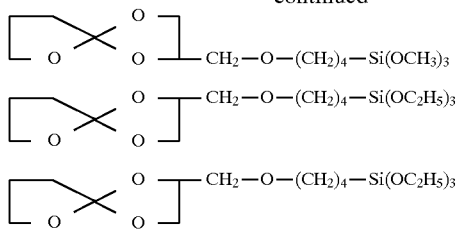

In preferred silanes of the general formula (II), X, R, $R^2$, A, n, k, l and x are defined as follows:

x=($C_1$–$C_4$)-alkoxy, preferably methoxy and ethoxy, or halogen, preferably chlorine;

R=($C_1$–$C_4$)-alkyl, preferably methyl and ethyl;

R2=($C_1$–$C_4$)-alkylene, preferably methylene and propylene;

A=O, S or NHC(O)O, preferably S;

n=1, 2 or 3 l=0 or 1, preferably 1;

4−(n+k)=0 for l=0 and 1 for l=1.

In the silanes of the general formula (II), it is particularly preferred if the structural unit having the index x is selected from triethoxysilyl, methyl-diethoxysilyl, methyldichlorosilyl, 3-methyldimethoxy-silylpropylthio, 3-triethoxysilylpropylthio, ethoxydimethylsilylmethylthio and methyldiethoxysilylmethylthio.

The radical B in the general formula (II) is derived from a substituted or unsubstituted compound B' having at least one or at least two C=C double bonds, for example vinyl, allyl, acrylic and/or methacrylic groups, and 5 to 50, preferably 6 to 30, carbon atoms. B is preferably derived from a substituted or unsubstituted compound B' having two or more acrylate and/or methacrylate groups. Compounds of this type are designated in the following as (meth)acrylates. If the compound B' is substituted, the substituents can be selected from among the abovementioned substituents. Compounds B' having two C=C double bonds are employed for the preparation of mono(meth)acryloxysilanes of the formula (II) and, for the preparation of poly(meth)acryloxysilanes of the formula (II), those having at least three C=C double bonds. Specific examples of compounds of this type are the following (meth)acrylates:

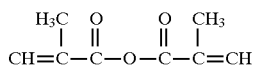

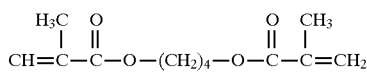

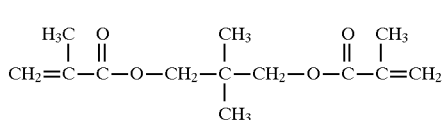

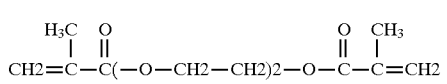

-continued
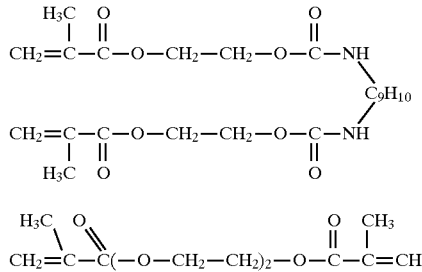
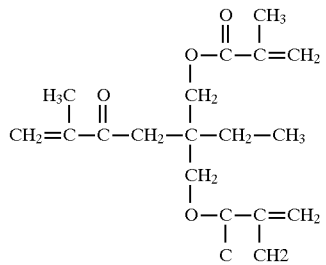
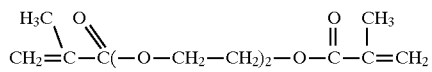
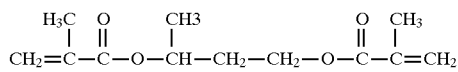
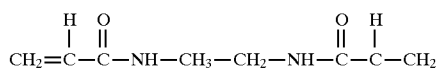
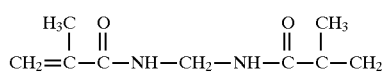
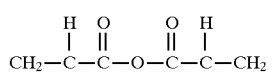
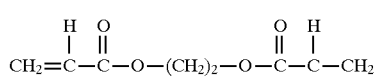
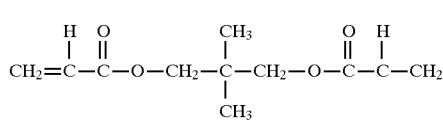
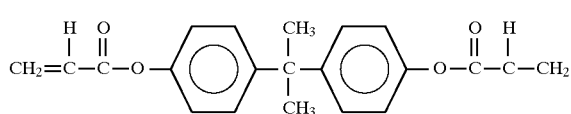

-continued
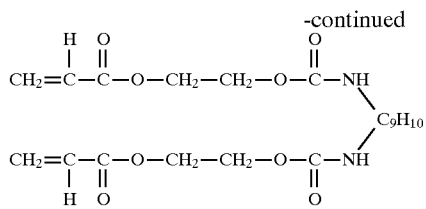
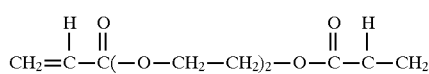
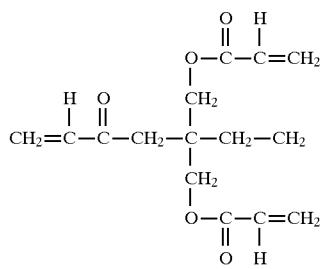
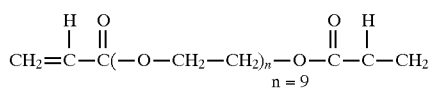
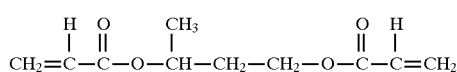
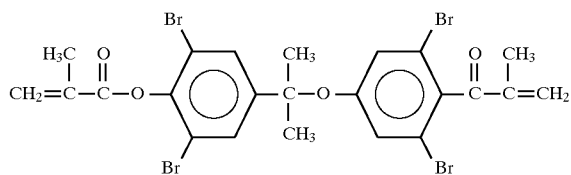
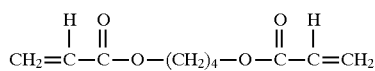
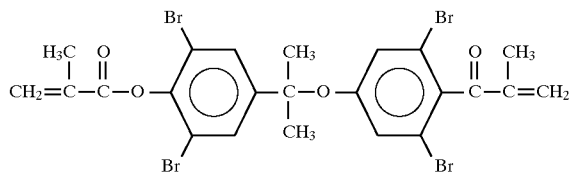
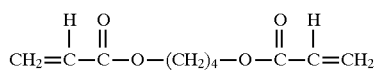
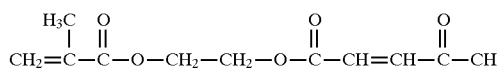
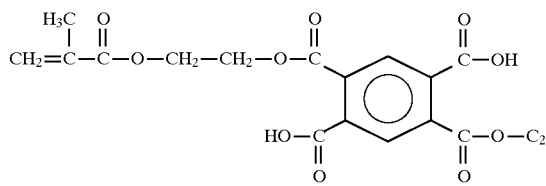
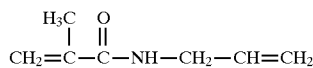
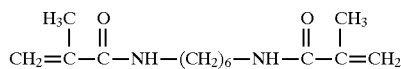

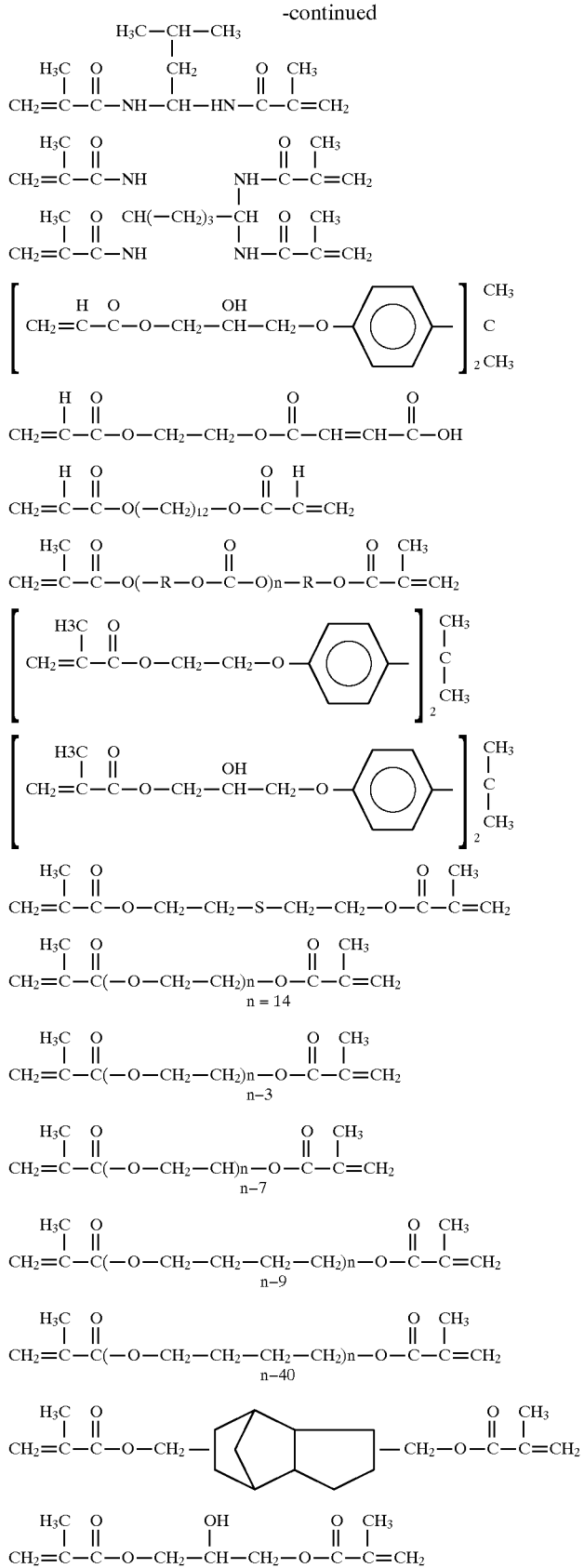

Preferred acrylates are, for example, the acrylic acid esters of trimethylolpropane, pentaerythritol and dipentaerythritol. Actual examples of these are trimethylolpropane triacrylate (TMPTA), pentaerythritol triacrylate (PETA), pentaerythritol tetraacrylate and dipentaerythritol pentaacrylate.

Further examples of preferred (meth)acrylates are those of the formula

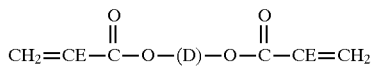

in which E represents H or CH3 and D is an organic group, such as is present, for example, in the abovementioned specific compounds and/or compounds described in the following examples.

Thus, D can be derived, for example, from $C_2$–$C_6$-alkanediols (for example ethylene glycol, propylene glycol, butylene glycol, 1,6-hexanediol), from polyethylene glycols or from polypropylene glycols (for example those of the formula HO—($CH^2$—$CHR^*$—O)$_i$H, in which R* is H or $CH_3$ and i=2–10) or from optionally substituted and/or alkoxylated (for example ethoxylated and/or propoxylated) bisphenol A.

The silanes of the general formula (I) are prepared, for example, by reaction of silanes of the general formula (IV)

 (IV)

with substituted or unsubstituted γ-butyrolactones in the presence of a Lewis acid and if appropriate in an inert, anhydrous solvent, the γ-butyrolactone being added in excess. The radicals X, Y' and R in the general formula (IV) are identical or different, X, R, n and m have the same meaning as in the silanes of the general formula (I), and Y' is a radical which represents a substituted oxirane ring. That stated above for the silanes of the general formula (I) applies to the possible embodiments of the radicals X and R.

Specific examples of silanes of the general formula (IV) are: glycidoxymethyltrimethoxysilane, glycidoxymethyltriethoxysilane, 2-glycidoxyethyltrimethoxysilane, 2-glycidoxyethyltriethoxysilane, 3-glycidoxypropyltrimethoxysilane, 3-glycidoxypropyltriethoxysilane, 3-glycidoxypropyl-tri(methoxyethoxy)silane, 3-glycidoxypropyltriacetoxysilane, 4-glyci-doxybutyltrimethoxysilane, 4-glycidoxybutyltrieth-oxysilane, glycidoxymethyl(methyl)-dimethoxysilane, glycidoxymethyl(ethyl)dimethoxysilane, glycidoxymethyl(phenyl)-dimethoxysilane, glycidoxymethyl(vinyl)-di-methoxysilane, glycidoxymethyl(dimethyl)-methoxy-silane, 2-glycidoxyethyl(methyl)dimethoxysilane, 2-gly-cidoxyethyl(ethyl)-dimethoxysilane, 2-glycidoxyethyl-(dimethyl)methoxysilane, 3-glycidoxypropyl(methyl)-di-methoxysilane, 3-glycidoxypropyl(ethyl)dimethoxysilane, 3-glycidoxypropyl(dimethyl)methoxysilane, 4-glycidoxybutyl(methyl)-dimethoxysilane, 4-glycidoxybutyl(ethyl)-dimethoxysilane, 4-glycidoxy-butyl-(dimethyl)-methoxysilane, bis(glycidoxymethyl)-dimethoxysilane, bis(glycidoxymethyl)diethoxysilane, bis(glycidoxy-ethyl)dimethoxy-silane, bis(glycidoxy-ethyl)-di-ethoxysilane, bis(glycidoxy-propyl)dimethoxysilane, bis(glycidoxypropyl)-diethoxysilane, tris-(glycidoxymethyl)methoxysilane, tris(glycidoxymethyl)-ethoxysilane, tris(glycidoxy-ethyl)methoxysilane, tris-(glycidoxyethyl)ethoxysilane, tris(glycidoxypropyl)-methoxysilane, tris(glycidoxy-propyl)ethoxysilane, glycidylmethyltrimethoxysilane, glycidylmethyl-triethoxysilane, 2-glycidylethyltrimethoxy-silane, 2-glycidylethyltriethoxysilane, 3-glycidylpropyl-trimethoxy-silane, 3-glycidylpropyltriethoxysilane, 3-glycidyl-propyltri-(methoxyethoxy)silane, 3-glycidyl-propyltri-acetoxysilane, 3,4-epoxycyclohexylmethyl-trimethoxysilane, 3,4-epoxy-cyclohexylmethyltriethoxysilane, 3,4-epoxycyclohexyl-ethyltrimethoxysilane, 3,4-epoxycyclohexylpropyltrimethoxysilane and 3,4-epoxycyclohexylbutyltrimethoxysilane.

Silanes of the general formula (IV) are commercially available, thus, for example, 3-glycidoxypropyldimethylethoxysilane, (3-glycidoxypropyl)-methyldiethoxysilane, 3-glycidoxypropyl-methyldiisopropenoxy-silane, (3-glycidoxypropyl)-trimethoxysilane, 2-(3,4-epoxycyclohexyl)-ethyltrimethoxysilane or (2-(3,4-epoxy-4-methylcyclohexyl)propyl)methyldiethoxy-silane at ABCR GmbH & Co.KG (Karlsruhe).

All these silanes can be converted with γ-butyrolactones into the corresponding spirosilanes of the general formula (I).

Suitable γ-butyrolactones for preparation of the spirosilanes of the general formula (I) are unsubstituted γ-butyrolactone, and also γ-butyrolactones substituted by hydroxyl, alkyl, alkenyl, aryl, alkylaryl, arylalkyl, alkylcarbonyl or alkoxycarbonyl groups.

The alkyl radicals are, for example, straight-chain, branched or cyclic radicals having 1 to 10 C atoms, and particularly preferably are lower alkyl radicals having 1 to 6 C atoms. Specific examples are methyl, ethyl, n-propyl, i-propyl, n-butyl, s-butyl, t-butyl, i-butyl, n-pentyl and n-hexyl.

The alkenyl radicals are, for example, straight-chain, branched or cyclic radicals having 2 to 10 carbon atoms, and particularly preferably are lower alkenyl radicals having 2 to 6 carbon atoms, such as, for example, vinyl, allyl or 2-butenyl.

Specific examples and preferred embodiments of Lewis acids are $BF_3.Et_2O$, $AlCl_3$ or $SnCl_4$.

The silanes of the general formula (IV) are reacted with the γ-butyrolactones to give the spirosilanes of the general formula (I) with exclusion of water, if appropriate in an inert solvent. For purification of the spirosilanes known techniques, such as, for example, high vacuum distillation, are used.

The preparation of the spirosilanes of the general formula (I) is schematically represented as exemplified by the reaction of γ-butyrolactoneslactone with (3-glycidoxypropyl)trimethoxysilane in the presence of $BF_3.Et_2O$.

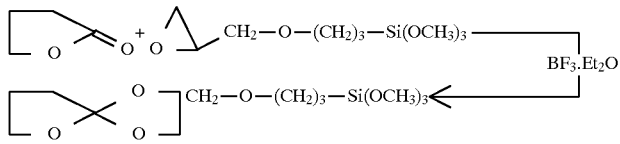

It is also possible additionally to modify the spirosilanes obtained according to the above reaction by known methods and to introduce other substituents, for example in the ring system which is derived from ■SYMBOL 103 \f "Symbol"■-butyrolactone. Thus, for example, Journal f.prakt.Chemie, Vol.330, No. 2, 1988, pp. 316–318 describes how methacrylic groups can be introduced into spirocyclic orthoesters in this ring system.

The silanes according to the general formula (II) can be prepared, for example, by a) subjecting a silane of the general formula (V)

$$X_n R_k SiR^2 Z \quad (V)$$

in which X, R, R², n and k have the abovementioned meaning, (n+k)=3 and Z denotes the group SH, PR'H or POR'H, to an addition reaction with a compound B' having at least two C=C double bonds; or b) subjecting a silane of the general formula (VI)

$$X''_n R^k SiR^2 NCO \quad (VI)$$

in which X, R, R², n and k have the abovementioned meaning and (n+k)=3, to a condensation reaction with a hydroxyl- or amino-substituted compound B' having at least one C=C double bond; or c) subjecting a silane of the general formula (VII)

$$X_n R_k SiH \quad (VII)$$

in which X, R, R², n and k have the abovementioned meaning and (n+k)=3, to a hydrosilylation reaction with a compound B' having at least two C=C double bonds.

The silanes of the general formulae (V) to (VII) are either commercially available or can be prepared by known methods; cf. W. Noll, "Chemie und Technologie der Silicone" (Chemistry and Technology of Silicones), Verlag Chemie GmbH, Weinheim/Bergstrasse (1968). In addition, reference is made to German Patent Application P 40 11 044.3.

The spirosilanes of the general formula (I) are stable compounds which are hydrolysable and condensable in basic medium without the Spiro complex being prematurely opened. In addition, reference is made to German Patent Application P 41 25 201.

The silanes of the general formulae (I) and/or (II) are processed either on their own or together with other hydrolytically condensable and optionally polymerisable components by means of hydrolytic condensation to give the resinous dental compositions according to the invention, whose final curing is then carried out by polymerisation of the polymerisable groups, in the case of the spirosilanes of the general formula (I) this polymerisation proceeding via ring opening of the 1,4,6-trioxaspiro(4.4)nonane groups and in the case of the silanes of the general formula (II) via linkage of the C=C double bonds of the radicals B.

The silanes of the general formulae (I) and (II) contain hydrolysable groups X, for example alkoxy groups, by means of which an inorganic network (Si—O—Si units) is constructed during the hydrolytic condensation, while the spiro groups contained in the radical Y or C=C double bonds contained in the radical B form an organic network during the polymerisation. The cured resinous dental compositions thus form an inorganic/organic matrix in which, when required, other components, such as, for example, fillers or pigments, can be incorporated.

For the construction of the inorganic network or for the preparation of the resinous dental compositions according to the invention, the spirosilanes of the general formula (I) and/or the silanes of the general formula (II) are hydrolysed and polycondensed by the action of water or moisture, if appropriate with the addition of other co-condensable components and if appropriate in the presence of a catalyst and/or of a solvent. This polycondensation is preferably carried out by the sol-gel process, as is described, for example, in DE-A1 2,758,414, 2,758,415, 3,011,761, 3,826, 715 and 3,835,968, and takes place in the presence of spiro compounds (silanes of the general formula (I), copolymerisable spiro-orthoesters, spiro-orthocarbonates, bicyclic spiro-orthoesters or methacryloyl spiro-orthoesters), preferably in basic medium, otherwise it can also be carried out in acidic medium.

For the construction of the organic network or for the curing of the dental materials, the resinous dental composition according to the invention, i.e. the polycondensate of the silanes of the general formulae (I) and/or (II) and if desired of further polycondensable components, is polymerised, if appropriate after addition of other copolymerisable components and/or after addition of fillers and/or of other additives, if appropriate in the presence of one or more initiators. The polymerisation can be carried out, for example, thermally or photochemically using customary methods.

The inorganic network is responsible for the fact that the cured resinous dental composition, entirely without the addition of fillers, already has an excellent resistance to abrasion, dimensional stability, polishing ability and adhesive force and a low thermal expansion coefficient, and the construction of the organic network causes the low or even negative shrinkage in volume. Owing to the number of spiro groups in the resinous dental composition according to the invention, i.e. owing to the type and/or owing to the amount of spirosilanes of the general formula (I) employed, the change in volume during the curing can be suited to the requirements of the particular application case. The higher the number of Spiro groups, the lower the shrinkage in volume. In fact it is even possible to influence the change in volume during the curing such that an increase in volume results.

The resinous dental compositions according to the invention comprise 1 to 100 mol %, preferably 5 to 100 mol %, based on monomeric compounds, of silanes of the general formulae (I) and/or (II). Besides these silanes, still other hydrolytically condensable compounds of silicon, boron, barium, aluminium, titanium, zirconium, tin, the transition metals, the lanthanides or actinides can be employed for the preparation of the resinous dental composition according to the invention. These compounds can either be used as such or even in pre-condensed form. It is preferred if at least 10 mol %, in particular at least 80 mol % and specifically at least 90 mol %, based on monomeric compounds, of the starting materials used for preparation of the resinous dental compositions according to the invention are silicon compounds.

It is also preferred if the resinous dental compositions according to the invention are based on at least 5 mol %, for example 25 to 100 mol %, in particular 50 to 100 mol % and specifically 75 to 100 mol %, in each case based on monomeric compounds, of one or more of the silanes of the general formulae (I) and/or (II).

Among the hydrolytically condensable silicon compounds other than silanes of the general formulae (I) and (II) which can optionally be employed, those of the general formula (III)

$$R_a(R''Z')_b SiX_{4-(a+b)} \qquad (III)$$

are particularly preferred in which the radicals R,R", X and Z' are identical or different and have the following meaning:

R=alkyl, alkenyl, aryl, alkylaryl or arylalkyl,

R"=alkylene or alkenylene, where these radicals can be interrupted by oxygen or sulphur atoms or NH groups, x=hydrogen, halogen, hydroxyl, alkoxy, acyloxy, alkylcarbonyl-, alkoxycarbonyl or $NR'_2$,
where R'=hydrogen, alkyl or aryl, Z'=halogen or an optionally substituted amino, amide, aldehyde, alkylcarbonyl, carboxyl, mercapto, cyano, alkoxy, alkoxycarbonyl, sulphonic acid, phosphoric acid, acryloxy, methacryloxy, epoxy or vinyl group, a=0, 1, 2 or 3, b=0, 1, 2 or 3, where a+b =1, 2 or 3.

Such silanes are described, for example, in DE 3,407,087 C2.

The alkyl radicals are, for example, straight-chain, branched or cyclic radicals having 1 to 20, preferably having 1 to 10, carbon atoms, and particularly preferably are lower alkyl radicals having 1 to 6 carbon atoms. Specific examples are methyl, ethyl, n-propyl, i-propyl, n-butyl, s-butyl, t-butyl, i-butyl, n-pentyl, n-hexyl, cyclohexyl, 2-ethylhexyl, dodecyl and octadecyl.

The alkenyl radicals are, for example, straight-chain, branched or cyclic radicals having 2 to 20, preferably having 2 to 10, carbon atoms, and particularly preferably are lower alkenyl radicals having 2 to 6 carbon atoms, such as, for example, vinyl, allyl or 2-butenyl.

Preferred aryl radicals are phenyl, biphenyl and naphthyl.

The alkoxy, acyloxy, alkylcarbonyl, alkoxycarbonyl and amino radicals are preferably derived from the abovementioned alkyl and aryl radicals. Specific examples are methoxy, ethoxy, n- and i-propoxy, n-, i-, s- and t-butoxy, methylamino, ethylamino, dimethylamino, diethylamino, N-ethylanilino, acetoxy, propionyloxy, methylcarbonyl, ethylcarbonyl, methoxycarbonyl, ethoxycarbonyl, benzyl, 2-phenylethyl and tolyl.

The said radicals can optionally carry one or more substituents, for example halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxyl, formyl, carboxyl, mercapto, cyano, nitro, epoxy, $SO_3H$ and $PO_4H_2$.

Among the halogens, fluorine, chlorine and bromine are preferred.

Specific examples of hydrolytically condensable silanes of the general formula (III) are:

$CH_3$—Si—$Cl_3$, $CH_3$—Si—$(OC_2H_5)_3$, $C_2H_5$—Si—$Cl_3$, $C_2H_5$—Si—$(OC_2H_5)_3$, $CH_2$=CH—Si—$(OC_2H_5)_3$, $CH_2$=CH—Si—$(OC_2H_4OCH_3)_3$, $(CH_3)_2$—Si—$Cl_2$, $CH_2$=CH—Si—$(OOCCH_3)_3$, $(CH_3)_2$—Si—$(OC_2H_5)_2$, $(C_2H_5)_3$—Si—Cl, $(C_2H_5)_2$—Si—$(OC_2H_5)_2$, $(CH_3)_2(CH_2$=CH)—Si—$Cl_2$, $(CH_3)_3$—Si—Cl, $(t-C_4H_9)(CH_3)_2$—Si—Cl, $(CH_3O)_3$—Si—$C_3H_6$—NH—$C_2H_4$—NH—$C_2H_4$—$NH_2$, $(CH_3O)_3$—Si—$C_3H_6$—SH, $(CH_3O)_3$—Si—$C_3H_6$—NH—$C_2H_4$—$NH_2$, $(CH_3O)_3$—Si—$C_3H_6$—Cl, $(CH_3O)_3$—Si—$C_3H_6$—O—C(O)—C($CH_3$)=$CH_2$, $(CH_3)_2(CH_2$=CH—$CH_2$)—Si—Cl, $(C_2H_5O)_3$—Si—$C_3H_6$—$NH_2$, $CH_2$=C($CH_3$) C(O)—O—$(CH_2)_3$—Si$(OCH_3)_3$, $(C_6H_5)_2$Si$(OCH_3)_2$, $CH_2$=C(H)—C(O)—O—$(CH_2)_3$—Si$(OCH_3)_3$, $(C_2H_5O)_3$—Si—$C_3H_6$—CN, $(CH_3O)_3$—Si—$C_3H_6$—O—$CH_2$—CH $CH_2$, $(CH_3O)_3$—Si—$(CH_2)_2$

Among the hydrolysable aluminium compounds optionally employed, those are particularly preferred which have the general formula (VIII)

$$AlR^*_3 \qquad (VIII)$$

in which the radicals $R^*$, which can be identical or different, are selected from halogen, alkoxy, alkoxycarbonyl and hydroxyl. With respect to the more detailed (preferred) definitions of these radicals, reference can be made to the embodiments in connection with the suitable hydrolysable silicon compounds. The groups just mentioned can also be completely or partially replaced by chelate ligands (for example acetylacetone or acetoacetic acid ester, acetic acid).

Particularly preferred aluminium compounds are the aluminium alkoxides and halides. In this connection, the following may be mentioned as actual examples:

Al$(OCH_3)_3$, Al$(OC_2H_5)_3$, Al$(O-n-C_3H_7)_3$, Al$(O-i-C_3H_7)_3$, Al$(OC_4H_9)_3$, Al$(O-i-C_4H_9)_3$, Al$(O-s-C_4H_9)_3$, $AlCl_3$, AlCl(OH)$_2$.

Compounds which are liquid at room temperature such as, for example, aluminium s-butoxide and aluminium i-propoxide, are particularly preferred.

Suitable hydrolysable titanium or zirconium compounds which can optionally be employed are those of the general formula (IX)

$$MX_yR_z \qquad (IX)$$

in which M denotes Ti or Zr, y is an integer from 1 to 4, in particular 2 to 4, z represents 0, 1, 2 or 3, preferably 0, 1 or 2, and X and R are defined as in the case of the general formula (I). This also applies to the preferred meanings. Particularly preferably, the compounds of the formula (IX) are those in which y is equal to 4.

As in the case of the above Al compounds, complexed Ti or Zr compounds can also be employed. Additional preferred complexing agents here are acrylic acid and methacrylic acid.

Actual examples of Zr and Ti compounds which can be employed are the following:

$TiCl_4$, Ti$(OC_2H_5)_4$, Ti$(OC_3H_7)_4$, Ti$(O-i-C_3H_7)_4$, Ti$(OC_4H_9)_4$, Ti(2-ethylhexoxy)$_4$, $ZrCl_4$, Zr$(OC_2H_5)_4$, Zr$(OC_3H_7)_4$, Zr$(O-i-C_3H_7)_4$, Zr$(OC_4H_9)_4$, Zr(2-ethylhexoxy)$_4$, $ZrOCl_2$.

Other hydrolysable compounds which can be employed for the preparation of the resinous dental compositions according to the invention are, for example, boron trihalides and boric acid esters, such as, for example, $BCl_3$, B$(OCH_3)_3$ and $B(OC_2H_5)_3$, tin tetrahalides and tin tetraalkoxides, such as, for example, $SnCl_4$ and $Sn(OCH_3)_4$ and barium compounds of thegeneral formula $BaR*_2$, in which R* represents alkoxy or acyloxy. Actual examples are $Ba(OCH_3)_3$, $Ba(OC_2H_5)_3$ or $Ba(OCOCH_3)$.

In this manner, it is possible to incorporate heavy elements, such as, for example, Zr, Ti or Ba into the resinous dental composition according to the invention in such a way that these are uniformly incorporated into the inorganic/organic network after curing. As a result, the X-ray opacity of the resinous dental composition according to the invention is increased compared to the resinous dental compositions according to the prior art, and dental materials based on the resinous dental compositions according to the invention are detectable in the X-ray image. This is of particular importance, for example in dental fillings.

The X-ray opacity of the resinous dental compositions according to the invention can also be increased by employing, for example, silanes of the general formula (II) whose radical B is derived from a bromine-substituted compound B'. Compounds B' of this type have already been enlarged upon in the description of the silanes of the general formula (II). It is also possible to add Br- or I-substituted, copolymerisable acrylates or methacrylates so that as a result of curing, i.e. as a result of polymerisation, the halogen is incorporated into the organic network. However, it is also possible to add Br- or I-substituted, hydrolysable silanes so that as a result of hydrolytic condensation the halogen is incorporated into the inorganic network.

The increase in the X-ray opacity of the resinous dental compositions according to the invention compared to those of the prior art means a considerable improvement in the prior art, since until now the necessary X-ray opacity has been adjusted by the addition of fillers.

The resinous dental compositions according to the invention can be prepared in the manner customary in the field of poly(hetero)condensates. If silicon compounds are virtually exclusively employed, the hydrolytic condensation can in most cases be carried out by directly adding the necessary water at room temperature or with slight cooling to the silicon compounds to be hydrolysed, which are either present as such or dissolved in a suitable solvent, (preferably with stirring and in the presence of a hydrolysis and condensation catalyst) and afterwards stirring the resulting mixture for some time (one hour to several hours).

In the presence of the reactive compounds of Al, Ti or Zr, as a rule stepwise addition of the water is recommended. Independently of the reactivity of the compounds present, the hydrolysis is as a rule carried out at temperatures between –20° and 130° C., preferably between 0° and 30° C. or the boiling point of the solvent optionally employed. As already indicated, the best manner of adding the water in particular depends on the reactivity of the starting compounds employed. Thus, for example, the dissolved starting compounds can be slowly added dropwise to an excess of water or water is added in one portion or in portions to the optionally dissolved starting compounds. It may also be useful not to add the water as such, but to introduce it into the reaction system with the aid of water-containing organic or inorganic systems. In many cases, the introduction of the amount of water into the reaction mixture with the aid of moisture-loaded adsorbents, for example molecular sieves, and water-containing organic solvents, for example 80% strength ethanol, has proven particularly suitable. The addition of water, however, can also be carried out by means of a chemical reaction in which water is set free during the course of the reaction. Examples of this are esterifications.

If a solvent is used, besides the lower aliphatic alcohols (for example ethanol or i-propanol), ketones, preferably lower dialkyl ketones, such as acetone or methyl isobutyl ketone, ethers, preferably lower dialkyl ethers, such as diethyl ether or dibutyl ether, THF, amides, esters, in particular ethyl acetate, dimethylformamide, amines, in particular triethylamine, and mixtures thereof are also suitable.

If spirosilanes of the general formula (I) are employed for the preparation of the resinous dental compositions according to the invention, the hydrolysis is preferably carried out in a medium which is basic with respect to these silanes. This is either produced by means of a basic solvent, such as, for example, triethylamine, or by addition of basic hydrolysis and condensation catalysts, such as, for example, NH3, NaOH, KOH, methylimidazole, etc.

The starting compounds do not necessarily already all have to be present at the start of the hydrolysis (polycondensation), but in certain cases it can even prove advantageous if only a part of these compounds is first brought into contact with water and the remaining compounds are added later.

In order to avoid as far as possible precipitations during the hydrolysis and polycondensation, in particular when using hydrolysable compounds other than silicon compounds, the addition of water can be carried out in several steps, for example in three steps. In this case, in the first step, for example, a tenth to a twentieth of the amount of water required for hydrolysis can be added.

After brief stirring, a fifth to a tenth of the necessary amount of water can be added and, after further brief stirring, the remainder can finally be added.

The condensation time depends on the respective starting components and their proportions, the catalyst optionally used, the reaction temperature, etc. In general, the polycondensation is carried out at normal pressure, but it can also be carried out at elevated or at reduced pressure.

The polycondensate thus obtained can either be employed as a resinous dental composition as such or after partial or nearly complete removal of the solvent used or of the solvent formed during the reaction and can be processed to give pasty dental materials which are photochemically and/or thermally curable in the presence of one or more initiators. In some cases, it may prove advantageous to replace the excess water and the solvent formed and optionally additionally employed by another solvent in the product obtained after the polycondensation in order to stabilise the polycondensate. For this purpose, the reaction mixture can be thickened, for example in vacuo at slightly elevated temperature (up to at most 80° C.) until it can still be taken up with another solvent without problems.

After addition of suitable initiators, the final curing of the resinous dental compositions according to the invention or of the dental materials resulting therefrom is carried out either thermally or photochemically in the case of one-component systems and by mixing the individual components in the case of self-curing multicomponent systems. In this way, in the course of a cationic polymerisation the rings of the spiro groups of the silanes of the formula (I) are opened and/or in the course of a free-radical polymerisation the C=C double bonds of the silanes according to the formula (II) are linked. In this way, the organic network is constructed. Surprisingly, it has been found that in the course of this polymerisation the volume of the resinous dental compositions according to the invention or of the dental materials resulting therefrom does not change or only changes slightly. Depending on the number of spiro groups of the silanes of the general formula (I) and if appropriate other spiro compounds added and/or depending on the number of groups B of the silanes of the general formula (II), an only slight decrease in volume, no change in volume or even an increase in volume is obtained, the decrease in volume becoming smaller with an increasing number of the spiro groups or of the groups B.

However, it is also possible to add other components polymerisable jonically and/or by free radicals to the resinous dental compositions according to the invention for the preparation of the dental materials before the final curing, i.e. before the polymerisation. Compounds polymerisable by free radicals which can be added are, for example, those having C=C double bonds, such as, for example, acrylates or methacrylates, the polymerisation taking place via the C=C double bonds. Ionically polymerisable compounds which can be added contain, for example, ring systems which are cationically polymerisable by ring opening, such as, for example, spiro-orthoesters, spiro-orthocarbonates, bicyclic spiro-orthoesters, mono- or oligoepoxides. However, compounds can also be added which are polymerisable both cationically and by free radicals, such as, for example, methacryloyl spiro-orthoesters. These are polymerisable by free radicals via the C=C double bond and cationically with ring opening. These systems are described, for example, in the Journal f.prakt. Chemie, Volume 330, No. 2, 1988, pp. 316–318, or in the Journal of Polymer Science: Part C: Polymer Letters, Vol. 26, pp. 517–520 (1988).

If the curing of the resinous dental composition according to the invention or of the dental materials resulting therefrom is carried out photochemically, customary cationic photoinitiators are added thereto. Suitable photoinitiators according to the prior art are, for example, compounds which on irradiation release acids, such as, for example, $C_6H_5-N_2BF_4$, $O-NO_2-C_6H_4-CH_2-O-SO_2CF_3$ or triarylsulphonium salts of the general formulae (X), (XI) and (XII)

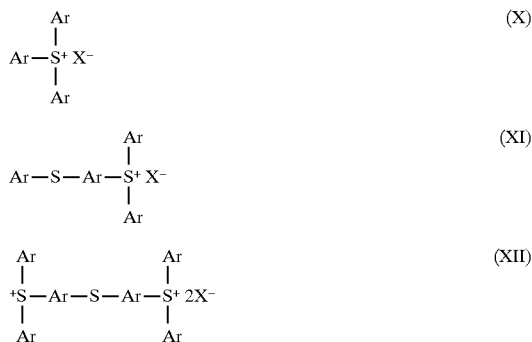

in which the radicals Ar can be identical or different and denote aryl or arylene, for example phenyl and phenylene, where $X-=BF_4-$, $AsF_6-$, $PF_6-$ or $SbF_6-$.

These photoinitiators are commercially available, for example triphenylsulphonium hexafluorophosphate as a 50% strength solution in propylene carbonate from Union Carbide under the trade name UVI-6990, or KI-85 (initiator according to formula (XII) where Ar=phenyl or phenylene and $X-=PF_6-$ as a 50% strength solution in propylene carbonate) from Degussa. In principle, however, all photoinitiators are suitable which are employed for the polymerisation of oxirane-containing molecules, such as, for example, cycloaliphatic epoxides.

The triarylsulphonium salt is subjected to photolysis under the influence of irradiation and a Broensted acid is formed which catalyses the ring opening of the spiro groups, the resinous dental composition polymerising.

If the curing of the resinous dental composition according to the invention or of the dental materials resulting therefrom is carried out thermally, thermal initiators are added thereto. Suitable thermal initiators are, for example, $BF_3$ as $BF_3.H_2NC_2H_5$, $ZnCl_2$, $TiCl_4$ or $SnCl_2$. Here also, all the thermal initiators which are suitable for the polymerization of epoxide groups can be employed.

The initiators are added in customary amounts.

The photoinitiators employed can be, for example, those commercially available. Examples of these are Iracure 184 (1-hydroxycyclohexyl phenyl ketone), Iracure 500 (1-hydroxycyclohexyl phenyl ketone/benzophenone) and other photoinitiators of the Iracure type obtainable from Ciba-Geigy; Darocure 1173, 1116, 1398, 1174 and 1020 (obtainable from Merck), benzophenone, 2-chlorothioxanthone, 2-methylthioxanthone, 2-isopropylthioxanthone, benzoin, 4,4'-dimethoxybenzoin, camphorguinone and others.

Suitable thermal initiators are in particular organic peroxides in the form of diacyl peroxides, peroxydicarbonates, alkyl peresters, dialkyl peroxides, perketals, ketone peroxides and alkyl hydroperoxides. Actual and preferred examples of thermal initiators are dibenzoyl peroxide, t-butyl perbenzoate and azobisisobutyronitrile.

The resinous dental compositions according to the invention can either be processed as such or together with the additives customary for dental materials described at the beginning, such as, for example, fillers, adhesion promoters or pigments to give pasty, photochemically and/or thermally curable dental materials. In this case, the advantageous properties already mentioned of the cured resinous dental compositions according to the invention are still further improved by addition of fillers, so that dental materials result therefrom whose property profile is very considerably improved compared to the prior art, and which can be aimed at all requirements which are made of such materials.

Fillers employed can be, for example, macrofillers (of glass, ceramic or quartz, particle sizes between 2 and 50 $\mu$m), homogeneous microfillers (for example of pyrogenic silica, particle sizes about 0.04 $\mu$m), inhomogeneous microfillers (a part of the pyrogenic silica is present as a chip polymer), hybrid fillers (mixture of macro- and microfillers) or very fine hybrid fillers (for example mixture of Aerosil and Ba or Sr glass with particle sizes of 2 $\mu$m). In this case, the mechanical properties of the resulting cured dental materials are additionally influenced by the particle size and the amount of the fillers. The shrinkage (the higher the filler content in the same matrix, the lower the shrinkage), the X-ray opacity (by addition of, for example, Ba, Sr, Ti or Zr components in the filler) and the thermal expansion coefficient (depending on the filler content; fillers usually have a lower expansion coefficient than the organic matrix) are also additionally positively influenced by the addition of fillers.

It is also possible to add cured resinous dental composition according to the invention for the preparation of dental materials to the uncured resinous dental compositions according to the invention in finely divided form as a filler. For this purpose, the resinous dental composition according to the invention is polymerised, for example in the form of an emulsion, a precipitation, a solution or a suspension polymerisation. The polymer is dried, optionally finely ground and added to the resinous dental composition.

The resinous dental compositions according to the invention can not only be processed to give photochemically and/or thermally curable dental materials, it is also possible to prepare the self-curing multicomponent systems mentioned at the beginning from the resinous dental compositions according to the invention.

The dental materials prepared from the resinous dental compositions according to the invention comprise 20 to 100% by volume of the resinous dental compositions according to the invention, the remaining amounts are optionally resinous dental compositions according to the prior art, fillers, pigments, initiators, other customary additives or further copolymerisable monomers, such as, for example, acrylates, methacrylates, mono- or oligoepoxides, vinyl ethers, spiro-orthoesters, spiro-orthocarbonates, bicyclic spiro-orthoesters or methacryloyl spiro-orthoesters. It is preferred if the resulting dental materials comprise 30 to 70% by volume of the resinous dental compositions according to the invention.

The resinous dental compositions according to the invention can also be employed either as such or in the form of solutions as adhesives or adhesion promoters to enamel and dentine, for the surface-sealing of conventional composites, as adhesion promoters for dental fillers and very generally as a coating composition in the dental field.

A great advantage of the resinous dental compositions according to the invention compared to the prior art is that in the case of polymerisable, toxic monomers, for example of toxic acrylates or methacrylates, these can be bonded firmly to the silanes of the formula (II) and are thus firmly embedded in the inorganic/organic network, so that even in the case of incomplete polymerisation after the curing of the resinous dental composition no free monomers can be present. In the resinous dental compositions according to the prior art, based on acrylates or methacrylates, there is, however, always the risk that after curing as a result of incomplete polymerisation free monomers are still present, which can lead to considerable toxic problems.

The invention is illustrated in greater detail with the aid of exemplary embodiments.

EXAMPLE 1

Preparation of 2-trimethoxysilylpropyl methyl ether-1,4,6-trioxaspiro(4.4)-nonane (Silane according to the general formula (I))

A solution of 307 g (1.3 mol) of 3-glycidyloxy-propyltrimethoxysilane in 300 ml of CH2Cl2 is added dropwise at room temperature under an argon atmosphere in the course of one hour to an initial mixture of 129 g (1.5 mol) of -butyrolactone and 4.62 g of boron trifluoride etherate ($BF_3.Et_2O$) in 600 ml of dried $CH_2Cl_2$. After stirring for about 2 hours at room temperature, the mixture is concentrated on a rotary evaporator and the residue is subjected to high vacuum distillation. After a preliminary fraction, the desired spirosilane is obtained at a temperature of about 125° C. ($2 \times 10^{-2}$ mbar) as a colourless, stable liquid.

IR: $\nu$(C—H) at about 2840–2969 $cm^{-1}$; $\nu$(C—H, methoxy) at 2480 $cm^{-1}$

EXAMPLE 2

Hydrolytic Condensation of 2-trimethoxy-silylpropyl methyl ether-1,4,6-trioxaspiro(4.4)nonane 20 mg of triethylamine and 0.54 g (30 mol) of H2O are added dropwise to 6.54 g (20 mol) of spirosilane according to Example 1 for the hydrolysis and condensation of the —Si(OCH$_3$)$_3$ groups. The mixture is stirred at room temperature for about 20 h. The resulting spirosiloxane is isolated after customary working up.

IR: $\nu$(C—H, methoxy) at 2480 $cm^{-1}$ no longer present →hydrolysis has taken place; $\nu$(C=O, ester) at 1738 $cm^{-1}$ not formed →spiro group not cleaved

EXAMPLE 3

Cationic Polymerisation of the Spirosiloxane from Example 2

The spirosiloxane according to Example 2 is treated with 2% starter (UVI 6990 from Union Carbide), applied to KBr discs, freed from all volatile constituents and irradiated with UV light (UV "Blue Point" point irradiator from Dr. K. Hönle), i.e. cured by polymerisation (complete conversion after <1 min).

IR: $\nu$(C=O, ester) at 1740 $cm^{-1}$ (intense band) →complete conversion and thus polymerisation of the spiro group →polyester siloxane

EXAMPLE 4

Cationic Polymerisation of the Spirosiloxane from Example 2

The spirosiloxane according to Example 2 is treated with 2% starter (KI-85 from Degussa) and applied to glass slides. For application, a film-drawing frame having various gap widths (30 and 80 $\mu$m) is used. The volatile constituents are removed, and curing is carried out by means of a "UVALOC 1000" UV irradiator from Loctite.

Using the starters according to Examples 3 and 4, hard, colourless compositions are obtained after exposure times of less than one minute.

EXAMPLE 5

Synthesis procedure for a resin system based on TMPTA and mercaptopropylmethyldimethoxysilane (ratio of 1:1)

72.14 g (0.4 mol) of mercaptopropylmethyldimethoxysilane are added dropwise under a protective gas atmosphere to an initial mixture of 118.5 g (0.4 mol) of trimethylolpropane triacrylate (TMPTA) in 400 ml of ethyl acetate. With cooling (ice-bath), a solution of 0.224 g (0.004 mol) of KOH in ethanol is slowly added dropwise. After about 5 minutes the reaction (thiol addition) is complete. 7.2 g of 0.7N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results. The viscosity is variable from 9,000 to 22,000 mPa·s at 25° C. by means of the synthesis conditions (resin system A).

EXAMPLE 6

Synthesis procedure for a resin system based on Ebercryl-53 and mercaptopropyl-methyldimethoxysilane (ratio 1:1)

54.1 g (0.3 mol) of mercaptopropylmethyldimethoxysilane are added dropwise under a protective gas atmosphere to an initial mixture of 128.5 g (0.3 mol) of glyceryl propoxytriacrylate (Ebercryl-53) in 270 ml of ethyl acetate. With cooling (ice-bath), a solution of 0.168 g (0.003 mol) of KOH in ethanol is slowly added dropwise. After about 5 minutes the reaction (thiol addition) is complete. 5.4 g of 0.7N HCl are added dropwise for the hydrolysis and condensation of the methoxy groups. Working up is carried out after stirring at room temperature for 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results. The viscosity is variable from 4,500 to 8,100 mpa·s at 25° C. by means of the synthesis conditions (resin system B).

EXAMPLE 7
Synthesis procedure for a resin system based on TMPTA and (mercaptomethyl)methyl-diethoxysilane (ratio of 1.2:1)

45.1 g (0.25 mol) of (mercaptomethyl)methyldiethoxysilane are added dropwise under a protective gas atmosphere to an initial mixture of 88.9 g (0.3 mol) of trimethylolpropane triacrylate (TMPTA) in 250 ml of ethyl acetate. With cooling (ice-bath), a solution of 0.140 g (0.0025 mol) of KOH in ethanol is slowly added dropwise. After about 1 minute, the reaction (thiol addition) is complete. 7.2 g of 0.5N HCl are added dropwise for the hydrolysis and condensation of the methoxy groups. working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results. The viscosity is variable from 4,200 to 7,000 mpa·s at 25° C. by means of the synthesis conditions (resin system C).

EXAMPLE 8
Synthesis procedure for a resin system based on TMPTA and (mercaptomethyl)methyl-diethoxysilane (ratio of 1:1)

0.4 mol of (mercaptomethyl)methyldiethoxysilane is added dropwise under a protective gas atmosphere to an initial mixture of 118.5 g (0.4 mol) of trimethylolpropane triacrylate (TMPTA) in 400 ml of ethyl acetate. With cooling (ice-bath), a solution of 0.224 g (0.004 mol) of KOH in ethanol is slowly added dropwise. After about 5 minutes the reaction (thiol addition) is complete. 7.2 g of 0.7N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results.

EXAMPLE 9
Synthesis procedure for a resin system based on TMPTA and (mercaptomethyl)-dimethylmethoxysilane (ratio 1:1)

0.3 mol of (mercaptomethyl)dimethylmethoxysilane is added dropwise under a protective gas atmosphere to an initial mixture of 0.3 mol of trimethylolpropane triacrylate (TMPTA) in 270 ml of ethyl acetate. With cooling (ice-bath), a solution of 0.168 g (0.003 mol) of KOH in ethanol is slowly added dropwise. After about 5 minutes the reaction (thiol addition) is complete. 5.4 g of 0.7N HCl are added dropwise for the hydrolysis and condensation of the methoxy groups. Working up is carried out after stirring at room temperature for 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results. The viscosity is variable from 900 to 7,200 mpa·s at 25° C. by means of the synthesis conditions (resin system E).

EXAMPLE 10
Synthesis procedure for a resin system based on TMPTMA and mercaptopropylmethyl-dimethoxysilane (ratio of 1:1)

18.03 g (0.1 mol) of mercaptopropylmethyldimethoxysilane are added dropwise under a protective gas atmosphere to an initial mixture of 33.84 g (0.1 mol) of trimethylolpropane trimethacrylate (TMPTMA) in 100 ml of ethyl acetate. With cooling (ice-bath), a solution of 0.56 g (0.01 mol) of KOH in ethanol is slowly added dropwise. After about 5 minutes the reaction (thiol addition) is complete. 1.8 g of 5.7N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent resin having a viscosity of about 1760 mpa·s at 25° C. results (resin system F).

EXAMPLE 11
Synthesis procedure for a resin system based on TMPTMA and mercaptopropyl-trimethoxysilane (ratio of 1:1)

9.82 g (0.05 mol) of mercaptopropyl-trimethoxysilane are added dropwise under a protective gas atmosphere to an initial mixture of 16.92 g (0.05 mol) of trimethylolpropane trimethacrylate (TMPTMA) in 50 ml of ethyl acetate. With cooling (ice-bath), a solution of 0.28 g (0.005 mol) of KOH in ethanol is slowly added dropwise. After about 1 minute the reaction (thiol addition) is complete. 2.16 g of 2.4N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent resin having a viscosity of about 16,000 mpa·s at 25° C. results (resin system G).

EXAMPLE 12
Synthesis procedure for a resin system based on BADMA and (mercaptomethyl)-methyldiethoxysilane (ratio of 1:1)

0.05 mol of (mercaptomethyl)methyldiethoxysilane is added dropwise under a protective gas atmosphere to an initial mixture of 0.05 mol of bisphenol-A-dimethacrylate (BADMA) in 50 ml of ethyl acetate. With cooling (ice-bath), a solution of 0.28 g (0.005 mol) of KOH in ethanol is slowly added dropwise. After about 1 minute, the reaction (thiol addition) is complete. 2.16 g of 2.4N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results (resin system H).

EXAMPLE 13
Synthesis procedure for a resin system based on Plex 6833-0 and mercaptopropyl-methyldimethoxysilane (ratio of 1:1)

0.05 mol of mercaptopropylmethyldimethoxysilane is added dropwise under a protective gas atmosphere to an initial mixture of 0.05 mol of ethoxylated bisphenol-A-dimethacrylate (Plex 6833-0) in 50 ml of ethyl acetate. With cooling (ice-bath), a solution of 0.28 g (0.005 mol) of KOH in ethanol is slowly added dropwise. After about 1 minute the reaction (thiol addition) is complete. 2.16 g of 2.4N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent resin having a viscosity of about 3,200 mpa·s at 25° C. results (resin-system I).

EXAMPLE 14
Synthesis procedure for a resin system based on TMPTA and (mercaptomethyl)-methyldiethoxysilane (ratio of 1.2:1) silanised with trimethylchlorosilane 45.1 g (0.25 mol) of (mercaptomethyl)-methyldiethoxysilane are added dropwise under a protective gas atmosphere to an initial mixture of 88.9 g (0.3 mol) of trimethylolpropane triacrylate (TMPTA) in 250 ml of ethyl acetate. With cooling (ice-bath), a solution of 0.140 g (0.0025 mol) of KOH in ethanol is slowly added dropwise. After about 1 minute, the reaction (thiol addition) is complete. 7.2 g of 0.5N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin which is silanised by customary methods with trimethylchlorosilane/triethylamine (for entraining the HCl set free) results. The viscosity is variable from 2,800 to 3,300 mpa·s at 25° C. by means of the synthesis conditions (resin system K).

The aim of the silanisation is the reaction of the free SiOH groups (hydrophilic centres in the resin) to reduce the absorption of water and thus to reduce the decrease in strength due to the addition of water, and to reduce the resin viscosity in order finally to ensure a higher filler content in the composite.

EXAMPLE 15
Synthesis procedure for a resin system based on TMPTA and (mercaptomethyl)methyldiethoxysilane and mercaptopropyltrimethoxysilane (ratio of 1.2:0.5:1)

0.125 mol of (mercaptomethyl)methyldiethoxysilane and 0.125 mol of mercaptopropyltrimethoxysilane are added dropwise under a protective gas atmosphere to an initial mixture of 88.9 g (0.3 mol) of trimethylolpropane triacrylate (TMPTA) in 250 ml of ethyl acetate. With cooling (ice-bath), a solution of 0.140 g (0.0025 mol) of KOH in ethanol is slowly added dropwise. After about 1 minute, the reaction (thiol addition) is complete. 7.2 g of 0.5N HCl are added dropwise for the hydrolysis and condensation of the methoxy groups. Working up is carried out after stirring at room temperature for about 20 hours by extracting by shaking, first with dilute, aqueous NaOH and finally with distd. water. After filtration, the filtrate is concentrated on a rotary evaporator. The volatile constituents are removed under an oil pump vacuum. A pale-yellow, transparent, viscous resin results (resin system M).

The resin viscosity, which is important for the workability (for example for the production of moulded articles and for the incorporation and the content of the fillers) can be varied within wide ranges, as is confirmed by these exemplary embodiments, with the same composition by means of the synthesis conditions and by the starting material combination and can thus be suited to the requirements of the particular application case.

EXAMPLE 16
Filler incorporation

As filler, a mixture of 30% of Aerosil OX50 (pyrogenic silica) and 70% of very fine glass GM 32087 (strontium silicate glass), both silanised, is incorporated into the resin system until a pasty consistency results. The incorporation can be carried out, for example, using the AM 501 universal mixer from Hauschild.

Resin system L1: Resin system K is mixed with 75% by weight (60% by volume) of the abovementioned filler mixture.

Resin system L2: Resin system B is mixed with 75% by weight (60% by volume) of the abovementioned filler mixture.

Resin system L3: Resin system I is mixed with 75% by weight (60% by volume) of the abovementioned filler mixture.

UV-cured moulded articles for other investigations are prepared from the resin systems A to M after addition of 1.0% of Iracure 184R as a UV initiator. Corresponding curing in the visible spectral range (after addition of, for example, camphorquinone as initiator) is likewise possible.

Other investigations and test conditions:

Breaking strength: The breaking strength is determined in a 3-point flexural test (UTS-100 universal testing machine) on rectangular rods (2×2×25 mm).

E Modulus: The E modulus is determined in a 3-point flexural test (UTS-100 universal testing machine) on rectangular rods (2×2×25 mm).

Shrinkage on curing: The shrinkage on curing is determined by means of the difference in thickness before and 24 h after curing.

Water absorption: The water absorption is determined on cylindrical moulded articles (1 mm thick with a diameter of 10 mm) after storage for 14 days in distd. water at 40° C. by final weighing (corrected for the water solubility).

Water solubility: The water solubility is determined on cylindrical moulded articles (1 mm thick with a diameter of 10 mm) after storage for 14 days in distd. water at 40° C. by final weighing.

Test results:

| Resin system: | A | B | C | D | E | F | G | H | | |
|---|---|---|---|---|---|---|---|---|---|---|
| E modulus [MPa]: | 1250 | 73 | 2150 | 2030 | 1140 | 500 | 1540 | 1470 | | |
| Resin system: | I | K | L1 | M | | | | | | |
| E modulus [MPa]: | <40 | 1690 | 8000 | 2100 | | | | | | |
| Resin system: | A | C | D | E | G | H | I | L1 | M | |
| Breaking strength [MPa]: | 63 | 90 | 86 | 60 | 65 | 65 | 70 | 120 | 95 | |
| Resin system: | A | B | C | E | I | K | L1 | L2 | L3 | M |
| Shrinkage on curing in [%]: | 7.0 | 4.9 | 7.8 | 5.4 | 1.7 | 7.0 | 2.9 | 2.0 | 0.7 | 6.9 |
| Resin system: | E | K | L | | | | | | | |
| Water absorption: | 1.4% | 1.3% | 0.6% | | | | | | | |
| Water solubility: | 0.1% | 0.0% | 0.0% | | | | | | | |

The shrinkage on curing can be reduced further by the use or by the addition of silanes of the general formula (I).

EXAMPLE 17

Preparation of a composite which is photochemically curable in the visible spectral range based on resin system K The following components are combined to give a pasty mixture:

| Resin system | |
|---|---|
| 2,2-Bis[4'-(2"-methacryloylethoxy)phenyl]- | K15.6 g |

The following components are combined to give a pasty mixture:

| | |
|---|---|
| Resin system | K15.6 g |
| 2,2-Bis(4'(2"methacryloylethoxy)phenyl)-propane | 6.44 g |
| 4-Methoxyphenyl | .007 g |
| Ethylbenzoin | 0.06 g |
| Camphorquinone | 0.10 g |
| 2-n-Butoxyethyl 4-(dimethylamino)benzoate | 0.13 g |
| Silanised strontium silicate glass | 54.4 g |
| Silanised, pyrogenic silica | 23.3 g |

After curing with a customary light source (Translux from Kulzer), the following values were measured:

| | |
|---|---|
| Flexural strength | 110 MPa |
| Water absorption | 0.57% |
| Shrinkage (after 24 h) | 2.3% |

EXAMPLE 18

Preparation of a self-curing composite based on resin system C

The following components are mixed to give a catalyst paste or to give a base paste:

| | Catalyst | Base |
|---|---|---|
| Resin system C | 15.6 g | 15.6 g |
| 2,2-Bis(4'-(2"-methacryloyl ethoxy)phenyl)propane | 6.44 g | 6.44 g |
| 4-Methoxyphenyl | 0.007 g | 0.007 g |
| N,N-Bis(2-hydroxyethyl)-p-toluidine | — | 2.0 g |
| Benzoyl peroxide | 2.0 g | — |
| Silanised strontium silicate glass | 54.4 g | 54.4 g |
| Silanised, pyrogenic silica | 21.55 g | 21.55 g |

The pastes are mixed and after curing the following values are measured:

| | |
|---|---|
| Flexural strength | 120 MPa |
| Water absorption | 0.68% |
| Shrinkage (after 24 h) | 2.3% |
| Processing time | 3 min |
| Setting time | 4 min 20 sec |

EXAMPLE 19

Preparation of a composite which is photochemically curable in the visible spectral range based on resin system K (without fillers)

The following components are combined to give a pasty mixture:

| | |
|---|---|
| Resin system | K70.0 g |
| 2,2-Bis(4'-(2"-methacryloylethoxy)phenyl) propane | 28.565 g |
| 4-Methoxyphenyl | .035 g |
| Ethylbenzoin | 0.30 g |
| Camphorquinone | 0.50 g |
| 2-n-Butoxyethyl 4-(dimethylamino)benzoate | 0.60 g |

After curing with a customary light source (Translux from Kulzer) the following values were measured:

| | |
|---|---|
| Flexural strength | 70 MPa |
| Compression strength | 352 MPa |
| Shrinkage (after 24 h) | 5.7% |

We claim:
1. A resinous dental composition, which is photochemically or thermally curable in the presence of initiators, or self curable in the presence of a redox catalyst, comprising/polymerisable polysiloxanes which are obtained by hydrolytic condensation of a) one or more hydrolytically condensable compounds of silicon; and b) if desired, elements selected from the group consisting of B, Ba, Ti, Zr, Al, Sn, and/or transition metals; and c) if desired, precondensates of the hydrolytically condensable compounds in (a) and/or the elements in (b);

if appropriate in the presence of a catalyst and/or of a solvent, by the action of water or moisture; wherein 1 to 100 mol % of the polymerisable polysiloxanes are based on monomeric compounds of silanes of the general formula (I)

$$Y_n SiX_m R_{4-(n+m)} \qquad (I)$$

in which the radicals X, Y and R are identical or different and have the following meaning:

R=alkyl, alkenyl, aryl, alkylaryl or arylalkyl,

X=hydrogen, halogen, hydroxyl, alkoxy, acyloxy, alkylcarbonyl, alkoxycarbonyl or NR'$_2$, where R'=hydrogen, alkyl or aryl, Y=a substituent which contains a substituted or unsubstituted 1,4,6-trioxaspiro (4.4) nonane radical n=1,2 or 3, m=1, 2 or 3, where n+m≦4;

and of silanes of the general formula (II)

$$\{X_n R_k Si(R^2(A)_l)_{4-(n+k)}\}_t D \qquad (II)$$

in which the radicals A, R, R$^2$ and X are identical or different and have the following meaning:

A=O, S, PR', POR', NHC(O)O or NHC(O)ONR', where R'=hydrogen, alkyl, or aryl,

D=a straight-chain or branched organic radical which is derived from a compound D' having at least one (for l=1 and A=NHC(O)O or NHC(O)NR') or at least two C=C double bonds and 5 to 50 carbon atoms, where R'=hydrogen, alkyl or aryl, R=alkyl, alkenyl, aryl, alkylaryl or arylalkyl, R$^2$=alkylene, arylene or alkylenearylene, X=hydrogen, halogen, hydroxyl, alkoxy, acyloxy, alkylcarbonyl, alkoxycarbonyl or NR'$_2$, where R'=hydrogen, alkyl or aryl, n=1, 2 or 3, k=0, 1 or 2 l=0 or 1, t=an integer whose maximum value corresponds to the number of double bonds in the compound D' minus 1, or is equal to the number of double bonds in the compound D' when l=1 and A represents NHC(O)O or NHC(O)NR'.

2. The resinous dental composition according to claim 1 wherein when said silanes of the general formula (I) are present at from about 5 mole % to about 100% mole % based on monomeric compounds.

3. Resinous dental composition according to claim 1, wherein the silanes of the general formula (I) are those in which Y is equal to

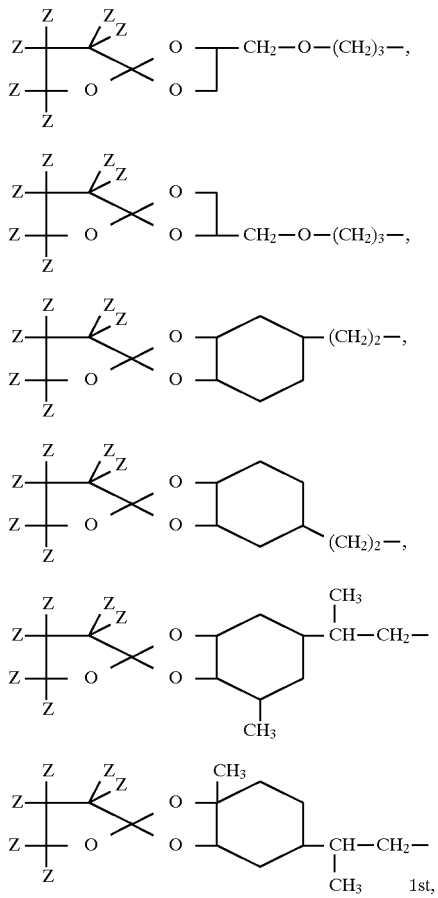

where the radical Z are identical or different and denote hydrogen, hydroxyl, alkyl, alkenyl, aryl, alkylaryl, arylalkyl, alkylcarbonyl, alkoxycarbonyl, acryloxy, methacryloxy or halogen.

4. Resinous dental composition according to claims 1, wherein the silanes of the general formula (II) are those in which the radicals and indices have the following meaning:

t=($C_1$–$C_4$)-alkoxy, preferably methoxy and ethoxy, or halogen, preferably chlorine;

R=($C_1$–$C_4$)-alkyl, preferably methyl and ethyl;

$R^2$=($C_1$–$C_4$)-alkylene, preferably methylene and propylene;

A=O or S;

n=1, 2 or 3;

l=0 or 1;

4−(n+k)=0 for l=0 and 1 for l=1; D and x formulated as in claim 1.

5. Resinous dental composition according to claim 3, wherein the silanes of the general formula (II) are those in which the unit having the index t is selected from triethoxysilyl, methyldiethoxysilyl, methyl-dichlorosilyl, 3-methyl-dimethoxysilylpropylthio, 3-triethoxysilylpropylthio, ethoxydimethylsilylmethylthio and methyldiethoxy-silylmethylthio.

6. Resinous dental composition according to claim 1 wherein the silanes of the general formula (II) are those in which the compound D' contains one (for l=1 and A=NHC(O)O or NHC(O)NR') C=C double bond.

7. Resinous dental composition according to claim 1, wherein the silanes of the general formula (II) are those in which the compound D' contains (for l=1 and A=NHC(O)O or NHC(O)NR') at least three C=C double bonds.

8. Resinous dental composition according to claim 1, wherein the silanes of the general formula (II) are those in which D is derived from a substituted or unsubstituted compound D' having two or more acrylate and/or methacrylate groups.

9. Resinous dental composition according to claim 7, wherein D is derived from acrylic acid esters or trimethylolpropane, pentaerythritol, dipentaerythritol, $C_2$–$C_6$-alkanediols, polyethylene glycols, polypropylene glycols or optionally substituted and/or alkoxylated bisphenol A.

10. Resinous dental composition according to claim 1, wherein the silanes of the general formula (II) are those in which t has the value 1 or 2.

11. Resinous dental composition according to claim 1, wherein the hydrolytically condensable compounds of silicon selected are one or more compounds of the general formula (III)

$$R_a(R''Z')_b SiX_{4-(a+b)} \qquad (III)$$

if appropriate in precondensed form, in which the radicals R, R" and Z' are identical or different and have the following meaning:

R=alkyl, alkenyl, aryl, alkylaryl or arylalkyl,

R"=alkylene or alkenylene, where these radicals can be interrupted by oxygen or sulphur atoms or NH groups, x=hydrogen, halogen, hydroxyl, alkoxy, acyloxy, alkylcarbonyl, alkoxycarbonyl or $NR'_2$, where R'=hydrogen, alkyl or aryl, Z'=halogen or an optionally substituted amino, amide, aldehyde, alkylcarbonyl, carboxyl, mercapto, cyano, alkoxy, alkoxycarbonyl, sulphonic acid, phosphoric acid, acryloxy, methacryloxy, epoxy or vinyl group, a=0, 1, 2 or 3, b=0, 1, 2 or 3, where a+b =1, 2 or 3.

12. Resinous dental composition according to claim 1, wherein the hydrolytically condensable components are selected from the group consisting of barium, titanium and zirconium compounds which are soluble in the reaction medium, if appropriate in precondensed form, of the general formula $$BaR''_2 \text{ or } MX_w R_u$$

in which M denotes titanium or zirconium, the radicals R", R and X are identical or different, R" represent alkoxy or acyloxy, w is an integer form 1 to 4, in particular 2 to 4, u represents 0, 1, 2 or 3, and x and R are defined as in the case of the general formula (I).

13. The resinous dental composition according to claim 12 wherein u represents 0, 1 or 2.

14. Resinous dental composition according to claims 1, wherein it additionally contains one or more monomers which are copolymerisable by free radicals and/or catonically.

15. Resinous dental composition according to claim 14, wherein it contains acrylates, methacrylates, mono- or oligoepoxides, vinyl ethers, spiro-orthoesters, spiro-orthocarbonates, bicyclic spiro-orthoesters or methacryloyl spiro-orthoesters as polymerisable monomers.

16. The resinous dental composition according to claim 1, comprising an adhesive or adhesion promoter to enamel and dentine, a coposition for the surface-sealing of conventional composites, an adhesion promoter for dental fillers and a coating composition in the dental field.

17. Pasty dental material, which is photochemically or thermally curable in the presence of initiators or self-curing, composed of one or more resinous dental compositions and, optionally, one or more finely divided fillers, comprising from about 20% to about 100% by volume of the resinous dental composition according to claim 1.

18. Pasty dental material, which is photochemically or thermally curable in the presence of initiators or self-curing, composed of one or more resinous dental compositions and, optionally, one or more finely divided fillers, comprising from about 20% to about 100% by volume of the resinous dental composition according to claim 2.

19. The pasty dental material according to claim 17 wherein said resinous dental composition is present at from about 30% to about 70% by volume.

20. The pasty dental material according to claim 18 wherein said resinous dental composition is present at from about 30% to about 70% by volume.

21. A pasty dental material according to claim 17, wherein an optional finely divided filler, if present, comprises a finely divided resinous dental composition according to claim 2.

22. The pasty dental material according to claim 17, wherein an optional finely divided filler, if present, comprises a finely divided resinous dental composition according to claim 3.

* * * * *